(12) United States Patent
Marzi et al.

(10) Patent No.: US 6,420,599 B2
(45) Date of Patent: Jul. 16, 2002

(54) CHEMICAL PROCESS FOR THE STEREOSELECTIVE SYNTHESIS OF R-(-)-CARNITINE

(75) Inventors: Mauro Marzi; Maria Ornella Tinti; Francesco De Angelis, all of Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 5 days.

(21) Appl. No.: 09/725,141

(22) Filed: Nov. 29, 2000

Related U.S. Application Data

(63) Continuation of application No. PCT/IT99/00138, filed on May 18, 1999.

(30) Foreign Application Priority Data

May 29, 1998 (IT) ...................................... RM98A0344

(51) Int. Cl.[7] .......................................... C07C 229/00
(52) U.S. Cl. ..................................................... 562/567
(58) Field of Search ......................................... 562/567

(56) References Cited

U.S. PATENT DOCUMENTS 4,413,412 A  * 11/1983  Fiorini et al.

FOREIGN PATENT DOCUMENTS

| EP | 0 609 643 | 8/1994 |
|----|-----------|--------|
| EP | 0 636 603 | 2/1995 |

OTHER PUBLICATIONS

Harmuth C. Kolb et al.: "Short and Practical Syntheses of (R)–(–)–Carnitine and (R)–(–)–gamma–Amino–beta–hydroxybutyric Acid (GABOB)" Tetrahedron: Asymmetry., vol. 4, No. 1 (Jan. 1993)pp. 133–141, Oxford GB.

Ching–Yun Hsu et al.: "Enantioselective Syntheses of (2S)–1–Benzyloxy–2,3–propanediol and (2R)–1–Amino–2, 3–propanediol from Glycerol" Tetrahedron: Asymmetry., vol. 1, No. 4, 1990, pp. 219–220 Oxford GB.

Hans–Peter Buser et al.: "Two Enantioselective Syntheses of the Diol Precursor of the Biologically Most Active Isomer of an insect Growth Regulator" Tetrahedron: Asymmetry., vol. 4, No. 12, (Dec. 1993) pp. 2451–2460, Oxford GB.

* cited by examiner

*Primary Examiner*—Gary Geist
*Assistant Examiner*—Paul Zucker
(74) *Attorney, Agent, or Firm*—Nixon & Vanderhye

(57) ABSTRACT

A process is described for the stereoselective synthesis of R-(–)-carnitine in which the characterizing step is condensation of glycerol with an amine of (–)camphorsulfonic acid.

1 Claim, 1 Drawing Sheet

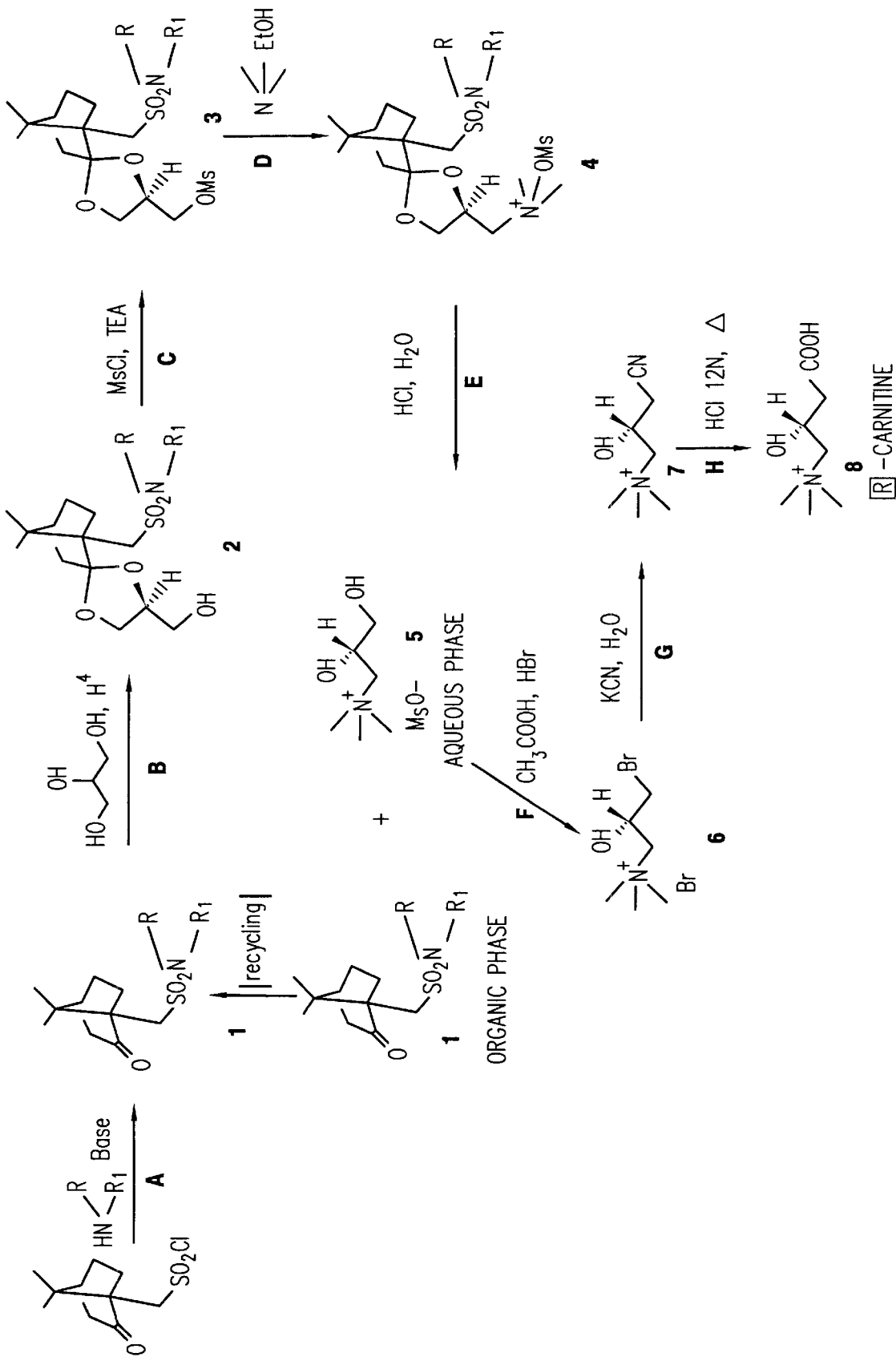

CHEMICAL PROCESS FOR THE STEREOSELECTIVE SYNTHESIS OF R-(-)-CARNITINE

This application is a continuation of PCT/IT99/00138 filed May 18, 1999.

The invention described herein relates to a chemical process for the stereoselective synthesis of R-(-)-carnitine.

BACKGROUND OF THE INVENTION

As is known, carnitine contains an asymmetry centre and can therefore exist in the form of two enantiomorphs, designated R-(-)-carnitine and S-(+)-carnitine, respectively. Of these, only R-(-)-carnitine is present in living organisms where it acts as a carrier for the transport of fatty acids across the mitochondrial membranes. Whereas R-(-)-carnitine is the physiologically active enantiomorph, for some years the R,S racemate has been used as a therapeutic agent. It has had to be acknowledged, however, that S-(+)-carnitine is a competitive inhibitor of carnitine acetyltransferase and can lower the levels of R-(-)-carnitine in the myocardium and in skeletal muscle.

It is therefore essential that only R-(-)-carnitine be administered to patients undergoing haemodialysis treatment or those under treatment for cardiac or lipid metabolism disorders.

The same principle applies to the therapeutic use of acylated derivatives of carnitine for the treatment of disorders of cerebral metabolism, peripheral neuropathies, peripheral arteriopathies, etc., for which acetyl R-(-)-carnitine and propionyl R-(-)-carnitine are used, obtained by acetylation of R-(-)-carnitine.

Various chemical processes have been proposed for the production of carnitine on an industrial scale. These processes are generally non-stereospecific and therefore lead to racemic mixtures of R and S enantiomorphs. Consequently, resolution methods must be used to separate the constituent enantiomorphs of the racemate. Typically, the R,S racemic mixture is reacted with an optically active acid, selected, for example, from D-tartaric acid or D-camphorsulfonic acid, obtaining two diastereoisomers that can be separated from each other. In the classic process described in U.S. Pat. No. 4,254,053, D-camphoric acid is used as the resolvent of a racemic mixture of R,S carnitinamide, obtaining S-(+)-carnitine as the waste product, while the R-(-)-carnitinamide is hydrolysed to R-(-)-carnitine.

These resolution processes are therefore complex and expensive and, in any case, lead to the production of both R-(-)-carnitine and an equal amount of S-(+)-carnitine or of a precursor with, however, the opposite configuration to that of R-(-)-carnitine, as a by-product.

In an attempt to use the substantial amount of S-(+)-carnitine (or of a precursor, such as S-(+),-carnitinamide), which is obtained as a waste product in the industrial production of R-(-)-carnitine, various processes have recently been proposed based on the stereospecific synthesis of R-(-)-carnitine starting from achiral derivatives (crotonobetaine or gamma-butyrobetaine) obtained precisely from this S-(+)-carnitine waste product.

These processes are generally based on the stereospecific hydration of crotonobetaine and differ from one another mainly in the particular micro-organism used to produce the biotransformation. See, for example, the processes described in: EP 0 121 444 (HAMARI), EP 0 122 794 (AJINOMOTO), EP 0 148 132 (SIGMA-TAU), JP 275689/87 (BIORU), JP 61067494 (SEITETSU), JP 61234794 (SEITETSU), JP 61234788 (SEITETSU), JP 61271996 (SEITETSU), JP 61271995 (SEITETSU), EP 0 410 430 (LONZA), EP 0 195 944 (LONZA), EP 0 158 194 (LONZA), EP 0 457 735 (SIGMA-TAU).

JP 62044189 (SEITETSU) describes a process for the stereoselective production of R-(-)-carnitine, starting, instead, from gamma-butyrobetaine, which in turn is obtained from crotonobetaine by an enzymatic method.

All these processes present drawbacks and are pose major technical problems.

In the first place, S-(+)-carnitine has to be converted to the achiral compound (crotonobetaine or gamma-butyrobetaine) which constitutes the starting product in all the aforementioned microbiological processes.

The latter present one or more of the following problems in production on an industrial scale:

(i) the R-(-)-carnitine yield is extremely low;
(ii) the micro-organisms must be grown on expensive nutrient media;
(iii) the micro-organisms support only low concentrations of crotonobetaine (up to 2–3% (w/v));
(iv) collateral reactions occur, such as, in the case of the use of crotonobetaine, for instance, the reduction of the latter to gamma-butyrobetaine, or the oxidation of R-(-)-carnitine to 3-dehydrocarnitine, which diminish the final R-(-)-carnitine yield.

More recently, a chemical process has been described (U.S. Pat. Nos. 5,412,113; 5,599,978; EP 0 609 643) based on the conversion to R-(-)-carnitine of a starting compound containing one asymmetric carbon atom with the opposite configuration to that of R-(-)-carnitine, without this compound having first to be converted to the achiral intermediate, crotonobetaine or gamma-butyrobetaine, and this achiral intermediate having to be later converted to R-(-)-carnitine. The starting compound consists in S-(+)-carnitinamide, which, as mentioned above, is obtained as a redundant waste product in the resolution of the R,S-carnitinamide racemic mixture by means of, for instance, D-camphoric acid. According to this process, the S-(+)-carnitinamide is converted to S-(+)-carnitine; the latter is esterified to protect the carboxyl group; the ester is acylated, preferably mesylated; after restoring the carboxyl group, the acyl derivative thus obtained is converted to a chiral lactone presenting the desired R configuration, which, through basic hydrolysis, supplies the R-(-)-carnitine.

It should be noted that both in the microbiological processes that obtain R-(-)-carnitine via an achiral intermediate and in the chemical process that enables R-(-)-carnitine to be obtained via chiral lactone, the starting product is a precursor of carnitine with the opposite configuration to that of the R form normally obtained by resolution of racemic mixtures, e.g. from R,S carnitinamide.

In other words, the basic assumption underlying all the above-mentioned, more recent processes is that to obtain R-(-)-carnitine it is above all necessary to continue using the chemical process consisting in resolution of R,S racemic mixtures, since it is this that produces, as a waste product, the carnitine precursor with the opposite configuration to that of the R form, which in the most up-to-date processes is precisely what constitutes the starting product. It certainly borders on the paradoxical that the most recent, technologically advanced processes for the production of R-(−)-carnitine should, for the purposes of their supply of starting products, continue to have to use the oldest process for the industrial production of R-(−)-carnitine.

The aim of the invention described herein is to provide a chemical process for the production of R-(−)-carnitine that does not start from a carnitine precursor with the opposite configuration to that of the R form, such as S-(+)-carnitinamide or S-(+)-carnitine.

In particular, the aim of the invention described herein is to provide a process for the production of R-(−)-carnitine which does without the continued use of processes based on the resolution of racemic mixtures of carnitine precursors, without which the starting compound for the above-mentioned, more recent processes would not be available.

It is also the aim of the invention described herein to provide a chemical process for the stereoselective synthesis of R-(−)-carnitine, the starting material of which is a simple achiral compound, which is easy to obtain at low cost, consisting in glycerol.

BRIEF DESCRIPTION OF THE DRAWING

FIG. 1 is a reaction scheme illustrating the process of the invention

DESCRIPTION OF THE INVENTION

The process according to the invention comprises the following stages:

(a) converting (−)camphorsulfonic acid chloride to (1R)-camphor-10-sulfonylamine 1 in which:
   R and $R_1$, which may be the same or different, are hydrogen or $C_1$–$C_4$ alkyl benzyl but cannot be both hydrogen; or
   R and $R_1$, together with the nitrogen atom to which they are bonded, form a heterocyclic group with 4–6 carbon atoms;
   reacting said chloride with a formula $HNRR_1$ amine, in which R and $R_1$ are as indicated above, chloride:amine molar ratio from 1:1.1 to 1:1.5, at 0° C.–30° C. for 2–4 hours;

(b) condensing sulfonylamine 1 with glycerol, glycerol:amine 1 molar ratio from 2:1 to 5:1, in an acid medium, obtaining (1R)-camphor-2-spirochetal glycerol- 10-sulfonylamine 2;

(c) mesylating sulfonylamine 2 by reacting 2 with methanesulfonyl chloride in a basic medium, molar ratio 1:1, at 0° C.–20° C., obtaining (1R)-camphor-2-(1-methanesulfonyl)spirochetal glycerol-10-sulfonylamine 3;

(d) substituting a trimethylammonium group for the mesyloxy group in 3, by reacting 3 with trimethylamine in an alcohol medium, 3:trimethylamine molar ratio from 1:20 to 1:1.5 at 25° C.–100° C., obtaining (1R)-camphor-2-(1-trimethylammonium)-spirochetal glycerol-10-sulfonyl-amine methanesulfonate 4;

(e) hydrolysing 4 in an acid medium, subsequently adding an organic solvent, obtaining an aqueous phase containing (R)-3-trimethylammonium-1,2-dihydroxy-propane methanesulfonate 5 and an organic phase containing amine 1 which is recycled to step (b);

(f) brominating 5 with hydrobromic acid in acetic acid, 5:HBr molar ratio from 1:6 to 1:1, for 15–24 hours at room temperature, subsequently adding an alkanol with 1–4 carbon atoms and refluxing the resulting mixture for 4–8 hours and then evaporating the mixture to dryness, obtaining (R)-3-trimethyl-ammonium-1-bromo-2-hydroxy-propane bromide 6;

(g) converting 6 to (R)-carnitine nitrile bromide 7, by reacting an aqueous solution of 6 with an equimolar amount of an alkaline cyanide for 5–24 hours at 25° C.–80° C. and then concentrating to dryness;

(h) converting 7 to R-(−)-carnitine inner salt 8 by reacting 7 with a concentrated acid at 60° C.–100° C. for 2–6 hours, then diluting the reaction mixture with water and eluting the aqueous solution thus obtained first on basic ion-exchange resin and then on acid resin.

In step (b), the acid medium is obtained by means of organic or inorganic acids such as acetic acid, trifluoroacetic acid, p-toluenesulfonic acid, pyridinium salt of p-toluenesulfonic acid, phosphoric acid, or sulfuric acid.

The acid preferred is p-toluenesulfonic acid.

In step (c), the basic medium is obtained by means of an organic base such as triethylamine, dimethylaminopyridine, isoquinoline, or quinoline. Triethylamine is preferred.

In step (d), the alcohol medium is obtained by means of alkanols such as methanol, ethanol, or isopropanol. Ethanol is preferred.

In step (e), the acid medium is obtained by means of aqueous solutions of hydrochloric acid, sulfuric acid, acetic acid, trifluoroacetic acid, or acid resins in the —$SO_3H$ form (Amberlite® IR-120, Amberlyst® 15, Dowex® 50). Aqueous HCl is preferred.

In step (e), the organic solvent is insoluble in water and is selected from the group consisting of ethyl acetate, ethyl ether, chloroform, and methylene chloride. Ethyl acetate and methylene chloride are the solvents preferred.

In step (f), the alkanol is selected from methanol or ethanol. Methanol is preferred.

In step (g), the cyanide salt is selected from the group consisting of sodium cyanide, potassium cyanide, and tetrabutylammonium cyanide. Sodium cyanide is preferred.

In step (h), the concentrated acid is, for example, hydrochloric acid 12N.

The basic ion-exchange resin is selected from the group consisting of Amberlite® IRA 402, IRA 410, Amberlyst® A-26, and Dowex® I-X8. Amberlite® IRA 402 is preferred.

The acid ion-exchange resin is selected from the group consisting of Amberlite® IRC-50, IRC-84, and Duolite® C433. Amberlite® IRC-50 is preferred.

The following examples, but not exclusively these, illustrate the process according to the invention.

EXAMPLE 1

Step (a)—Preparation of: (1R)-camphor-10-sulfonylpyrrolidine 7.11 g of pyrrolidine (100 mmol) and 13 g of 4-dimethylaminopyridine (111 mmol) were dissolved in a flask in 200 ml of methylene chloride. 26 g of (−)camphorsulfonyl chloride solubilised in 20 ml of methylene chloride were added dropwise to the solution at 0° C.

After approximately 30 minutes, at the end of the reaction, 800 ml of ethyl acetate and 100 ml of water were added. After separating the aqueous phase, the organic phase was further agitated first with HCL 1N three times and then with water. After drying on anhydrous $Na_2SO_4$, the organic phase was vacuum-concentrated. The crude product thus obtained was purified by silica gel chromatography. The solid was crystallised by means of hexane (23.7 g yield=80%).

TLC=hexane/AcOEt 7:3, Rf=0.29

MP=76° C.–77° C.

$[\alpha]_D$=−34.80 ( 1% $CHCl_3$)

$^1$H-NMR-300 Mhz($CDCl_3$); δ3.40–3.20(5H,m,2$CH_2$,CH); 2.80–2.70 (1H,d,CH); 2.59–2.41 (1H,m,CH); 2.49–2.22 (1H,dt,CH); 2.30–1.80 (7H,m,3CH,2$CH_2$); 1.62–1.49(1H,m,CH); 1.42–1.25(1H,m,CH); 1.30(3H,s,$CH_3$); 0.81(3H,s,$CH_3$).

Elemental Analysis=meets standards for $C_{14}H_{23}NO_3S$

Step (b)—Preparation of: (1R)-camphor-2-spirochetal glycerol-10-sulfonylpyrrolidine In a flask equipped with coolant and soxhlet (loaded with activated molecular sieves), 10 g (35 mmol) of the compound obtained in the previous step, 2.3 g of anhydrous glycerol (70 mmol) and 0.5 g of p-toluenesulfonic acid were suspended in 100 ml of anhydrous benzene. The reaction mixture was left to reflux for 3 days. At the end of refluxing, after cooling, the mixture was diluted with AcOEt and the organic phase washed with a saturated solution of $NaHCO_3$. The organic phase was then dried on anhydrous $Na_2SO_4$ and concentrated to dryness. The crude product was subjected to flash chromatography. 7.2 g of product (yield 60%) were $^1$H-NMR-300 Mhz($CDCl_3$); δ4.50–4.40(1H,m,CH); 4.25–4.20(2H,m,$CH_2$); 4.00–3.90(1H,t,CH); 3.70–3.60(1H,t,CH); 3.30–3.10(5H,m,2$CH_2$,CH); 3.00 (3H,s,$CH_3$); 2.60–2.50(1H,d,CH); 2.30–2.10 (1H,m,CH); 2.00–1.80(1H,m,CH); 1.80–1.60(7H,m,3CH,2$CH_2$); 1.44–1.40(1H,d,CH); 1.30–1.10(1H,m,CH); 0.94(3H,s,$CH_3$); * 0.84(3H,s,$CH_3$). obtained as oil, together with 3 g of starting ketone, and 2.5 g of impurities, including the other diastereoisomer.

TLC=hexane/AcOEt 7:3, Rf=0.15

$[\alpha]_D$=+11.84° (1% $CHCl_3$)

$^1$H-NMR-300 Mhz ($CDCl_3$); δ4.08–3.88(4H,m,2$CH_2$); 3.44–3.90(2H,d,2CH); 3.37–3.20(4H,m,2$CH_2$); 2.62–2.46 (1H,d,CH); 2.34–2.20(1H,m,CH); 2.1–1.68(8H,m,4CH,2$CH_2$); 1.43–1.39(1H,d,CH); *1.32–1.18(1H,m,CH); 0.92 (3H,s,$CH_3$); 0.85(3H,s,$CH_3$).

Elemental Analysis=meets standards for $C_{17}H_{29}NO_5S$

Step (c)—Preparation of: (1R)-camphor-2-(1-methanesulfonyl)-spirochetal glycerol-10-sulfonylpyrrolidine To the 17 g (50 mmol) chloroform solution of the product synthesised in the previous step were added first triethylamine (10.6 ml, 75 mmol) and then methanesulfonyl chloride (5 ml, 75 mmol) dropwise at 0° C. After a few hours the reaction mixture was washed agitating the solution first with HCl 1N, then with a saturated solution of $NaHCO_3$ and lastly with water. The organic solution was dried on anhydrous $Na_2SO_4$ and concentrated to dryness. A crude oil was obtained, which was further purified by silica gel chromatography. 19 g of product (yield 90%) were obtained.

TLC=hexane/AcOEt 7:3 Rf=0.19

$[\alpha]_D$32 +12.57° (1% $CHCl_3$)

Elemental Analysis=meets standards for $C_{18}H_{31}NO_7S_2$

Step (d)—Preparation of: (1R)-camphor-2-(1-trimethylammonium)-spirochetal glycerol-10-sulfonylpyrrolidine methanesulfonate 16.8 g (40 mmol) of the compound produced in the previous step were directly dissolved in 200 ml of a solution of 33% trimethylamine. The reaction was interrupted after 48 hours at 50° C., removing the solvent under reduced pressure. A crude product was obtained, which, after purification by silica gel chromatography, yielded 19 g of product (yield 99%).

TLC=$CHCl_3$/IsPrOH/MeOH/$H_2O$/$CH_3COOH$ (4.2/0.7/2.8/1.05/1.05)

Rf=0.66

$[\alpha]_D$=−13.5° (1% MeOH)

$^1$H-NMR-300 Mhz(MeOD); δ4.53–4.50(1H,m,CH); 4.25–4.15(1H,m,CH); 3.9–3.75(1H,dd, CH); 3.75–3.65(1H, t,CH); 3.60–3.50(1H,d,CH); 3.40–3.10(14H,m,2$CH_2$,CH, 3$CH_3$); 2.80–2.72(1H,d,CH); 2.70(3H,s,$CH_3$); 2.30–2.20 (1H,m,CH); 2.20–2.10(1H,m,CH); 1.80–1.60(7H, m,3CH, 2$CH_2$): 1.52–1.50(1H,d,CH); 1.40–1.20(1H,m,CH); 1.05 (3H,s,$CH_3$); 0.95(3H,s,$CH_3$).

Elemental Analysis=meets standards for $C_{21}H_{40}N_2O_7S_2$

Step (e)—Preparation of: (R)-3-trimethylammonium-1,2-dihydroxy-propane methanesulfonate and Recovery of (1R)-camphor-10-sulfonylpyrrolidine 19 g (39.6 mmol) of the ammonium salt obtained in the previous step were solubilised in 200 ml of methanol with 30 ml of HCl 3N. This was left to react for 18 hours at 70° C., whereupon the solution was concentrated. The semisolid obtained was re-dissolved in ethyl acetate and water. After a brief period of agitation of the phases and their separation, both were dried. (1R)-Camphor-10-sulfonylpyrrolidine was obtained from the organic phase, whereas the titre product was obtained from the aqueous phase. This was re-dissolved in water and decolourised with carbon. After once more drying out the solution, a very hygroscopic semisolid was obtained (9 g, yield 99%).

TLC=$CHCl_3$/IsPrOH/MeOH/$H_2O$/$CH_3COOH$ (4.2/0.7/2.8/1.05/1.05)

Rf=0.14

HPLC=Hypersil-APS; eluent: $NH_4H_2PO_4$ 0.1 M 35/$CH_3CN$ 65; pH=6.0; detectors: UV 205 nm; RI; RT=7.76

$[\alpha]_D$=−18° (1% $H_2O$)

1H-NMR-300 Mhz($D_2O$); δ4.20–4.10(1H,m,CH); 3.48–3.42(2H,d,$CH_2$); 3.38–3.22(2H,m,$CH_2$); 3.05(9H,s, 3$CH_3$); 2.62(3H,s,$CH_3$).

$H_2O$=2.6%

Fab-Ms (+)=134

Elemental Analysis=meets standards for $C_7H_{19}NO_5S$

Step (f)—Preparation of: (R)-3-trimethylammonium-1-bromo-2-hydroxy-propane bromide 9 g (39 mmol) of (R)-3-trimethylammonium-1,2-dihydroxy-propane-methanesulfonate and 25 ml of acetic anhydride were dissolved in 160 ml of HBr (30% acetic acid solution) and left to react for 24 hours at room temperature. 700 ml of methanol were then added and the resulting solution was left to reflux for another 6 hours. The solution was concentrated and the resulting oil was solidified by treating it several times with ethyl ether. The solid was further purified by acetone crystallisation. 9.8 g of product were obtained as a yellowish solid with a yield of 90%.

TLC=CHCl$_3$/IsPrOH/MeOH/H$_2$O/CH$_3$COOH (4.2/0.7/2.8/1.05/1.05)

Rf=0.20

HPLC=Hypersil-APS; eluent: NH$_4$H$_2$PO$_4$=0.1 M 35/CH$_3$CN 65; pH=3.0; detectors: UV 205 nm; RI; RT=4.53 min.

$[\alpha]_D$=−15.7° (1% H$_2$O)

$^1$H-NMR-300 Mhz(D$_2$O); δ4.5−4.38(1H,m,CH); 3.50−3.30(4H,d,2CH$_2$); 3.10(9H,s,3CH$_3$).

H$_2$O=1%

Fab-Ms (+)=196, 198

Elemental Analysis=meets standards for C$_6$H$_6$Br$_2$ NO

Step (a)—Preparation of (R)-carnitine nitrile bromide

To the compound obtained in the previous reaction (8 g, 28.7 mmol), dissolved in water, were added 1.886 g of potassium cyanide (28.7 mmol). The solution was kept at 70° C. for 24 hours. The water was removed by distillation. The crude solid obtained was tested and proved to be a 50% mixture of carnitine nitrile bromide and potassium bromide.

HPLC=Sperisorb-SCX; eluent: KH$_2$PO$_4$ 50 mM 60%/CH$_3$CN 40%; pH=3.0; detectors: UV 205 nm; RI; RT=13.73 min.

$^1$H-NMR-300 Mhz(D$_2$O); δ4.6−4.50(1H,m,CH); 3.40−3.30(2H,m,CH$_2$); 3.10(9H,s,3CH$_3$); 2.60−2.42(2H,m,CH$_2$).

Step (h)—Preparation of (R)-carnitine Inner Salt

The crude carnitine nitrile obtained in the previous reaction was dissolved at room temperature in 12 ml of 37% HCL 12N. The solution was heated at 90° C. for 4 hours. At the end of heating, the resulting black solution was diluted with 20 ml of water and eluted first on Amberlite IRA-402 resin (activated in the OH$^−$ form) and then on Amberlite IRC-50 resin (activated in HCl form). The eluate was concentrated and the 4 g of solid thus obtained were crystallised with isopropyl alcohol (white solid, 3.7 g, yield 80%).

HPLC=SGE-SCX; eluent: KH$_2$PO$_4$ 50 mM 60%/CH$_3$CN 40%; pH=3.0; detectors: UV 205 nm; RI; RT=16.5 min

H$_2$O=0.7%

$[\alpha]_D$=−3.90° (1% H$_2$O)

$^1$H-NMR-300 Mhz (D$_2$O); δ4.62−4.50(1H,m,CH); 3.50−3.40(2H,m,CH$_2$); 3.25(9H,s,3CH$_3$); 2.60−2.42(2H,m,CH$_2$).

Elemental Analysis=meets standards for C$_7$H$_{15}$NO$_3$

EXAMPLE 2

Step (a)—Preparation of: (1R)-camphor-10-sulfonyldibenzylamine

The product was synthesised according to the processes described in Example 1, step (a), with a yield of 80%.

TLC=hexane/AcOEt 7:3, Rf=0.58

MP=73–75° C.

$[\alpha]$D=−24.7° (0.6% MeOH)

$^1$H-NMR-300 Mhz (CDCl$_3$); δ7.40−7.20(1OH,m, aromatic); 4.60−4.20(4H,dd, 2CH$_2$); 3.40−3.20(1H,d,CH); 2.70−2.50(1H,d,CH);2.59−2.50(1H,m,CH);2.40− 2.30(1H, m,CH); 2.10−1.90(2H,m,2CH); 2.00−1.80(1H,d,CH); 1.80−1.60(1H, m,CH); 1.42−1.25(1H,m,CH); 1.10(3H,s, CH$_3$); 0.80(3H,s, CH$_3$).

Elemental Analysis=meets standards for C$_{24}$H$_{29}$NO$_3$S

Step (b)—Preparation of: (1R)-camphor-2-spirochetal glycerol-10-sulfonyldibenzylamine The product was synthesised according to the processes described in Example 1, step (b), with a yield of 42.5%.

TLC=hexane/AcOEt 7:3, Rf=0.46

DSC analysis=74.4%

$[\alpha]_D$=+1.2° (1% CHCl$_3$)

$^1$H-NMR-300 Mhz (CDCl$_3$); δ7.40−7.20(10H,m, aromatic); 4.60−4.10(4H,dd, 2CH$_2$); 4.10−3.80(4H,m,4CH); 3.50−3.40(1H,m,CH);3.30−3.20(1H,d,CH); 2.40−2.30(1H, d,CH); 2.40−2.20(1H,m,CH); 2.10−1.90(2H,m,2CH); 1.80−1.60(2H, m,2CH); 1.42−1.38(1H,d,CH); 1.30−1.10 (1H,m,CH); 1.10(3H,s,CH$_3$); 0.80(3H, s,CH$_3$).

Elemental Analysis=meets standards for C$_{27}$H$_{35}$NO$_5$S

Step (c)—Preparation of: (1R)-camphor-2-(1-methanesulfonyl)-spirochetal glycerol-10-sulfonyldibenzylamine The product was synthesised according to the processes described in Example 1, step (c), with a yield of 95%.

TLC=hexane/AcOEt 18:15, Rf=0.10

$[\alpha]_D$=+2.70 (2% CHCl3)

$^1$H-NMR-300 Mhz(CDCl$_3$); δ7.40−7.20(10H,m, aromatic); 4.60−4.40(1H,m, CH); 4.35−4.20(4H,dd,2CH$_2$); 4.30−4.10(2H,m,2CH); 4.00−3.40(1H, CH); 3.65−3.55(1H, t,CH); 3.15−3.05(1H,d,CH); 3.00(3H,s,CH$_3$); 2.40−2.30 (1H,d, CH); 2.28−2.20(1H,m,CH); 2.00−1.90(1H,m,CH); 1.82−1.60(3H,m,3CH); 1.42−1.38(1H,d,CH); 1.30−1.10 (1H,m,CH); 0.80(3H,s,CH$_3$); 0.68(3H,s,CH$_3$).

Elemental Analysis=meets standards for C$_{28}$H$_{37}$NO$_7$S$_2$

Step (d)—Preparation of: (1R)-camphor-2-(1-trimethylammonium)-spirochetal glycerol-10-sulfonyldibenzylamine methanesulfonate The product was synthesised according to the processes described in Example 1, step (d), with a yield of 97%.

TLC=CHCl$_3$/IsPrOH/MeOH/H$_2$O/CH$_3$COOH (4.2/0.7/2.8/1.05/1.05)

Rf=0.95

$[\alpha]_D$=−7.3° (1% MeOH)

Fab-Ms=527

$^1$H-NMR-300 Mhz (MeOD); δ7.40−7.20(10H,m, aromatic); 4.65−4.55(1H,m, CH); 4.40−4.30(4H,d,2CH$_2$); 4.20−4.10(1H,t,CH); 3.90−3.80(1H,dd,CH); 3.75−3.65(1H, t,CH); 3.51−3.50(1H,d,CH); 3.40−3.2(2H,m,2CH); 3.50 (9H,s, 3CH$_3$); 2.70(3H,s,CH$_3$); 2.50−2.40(1H,d,CH); 2.30−2.20(1H,m,CH); 2.10−2.00(1H,m,CH); 1.90−1.70(2H, m,2CH); 1.60–1.50(1H,d,CH); 1.40–1.30(1H,m,CH); 0.80 (3H,s,CH$_3$); 0.68(3H,s,CH$_3$).

Elemental Analysis=meets standards for C$_{31}$H$_{46}$NO$_7$S$_2$

Step (e)—Preparation of: (R)-3-trimethylammonium-1,2-dihydroxy-propane methanesulfonate and Recovery of (1R)-camphor-10-sulfonyldibenzylamine The product was synthesised according to the processes described in Example 1, step (e).

Stages (f)–(h)

The products were synthesised according to the processes described in Example 1, stages (f)–(h).

EXAMPLE 3

Step (a)—Preparation of: (1R)-camphor-10-sulfonyldimethylamine

The product was synthesised according to the processes described in Example 1, step (a), with a yield of 72%.

TLC=hexane/AcOEt 7:3, Rf=0.38

MP=62°–63° C.

$[\alpha]_D$=−35.4° (1% CHCl$_3$)

$^1$H-NMR-300 Mhz(CDCl$_3$); δ3.30–3.20(1H,d,CH); 2.82 (6H,s,2CH$_3$); 2.70–2.60(1H,d,CH); 2.50–2.40(1H,m,CH); 2.38–2.24(1H,m,CH); 2.10–1.90(2H,m,2CH); 1.90–1.80 (1H,d,CH); 1.60–1.50(1H,m,CH); 1.42–1.25(1H,m,CH); 1.10(3H,s,CH$_3$); 0.80(3H,s,CH$_3$).

Elemental Analysis=meets standards for C$_{12}$H$_{21}$NO$_3$S

Step (b)—Preparation of: (1R)-camphor-2-spirochetal glycerol-10-sulfonyldimethylamine The product was synthesised according to the processes described in Example 1, step (b), with a yield of 50%.

TLC=hexane/ethyl ether 6:4 Rf=0.18

$[\alpha]_D$=+13.1° (2% CHCl$_3$)

$^1$H-NMR-300 Mhz(CDCl$_3$); δ4.10–3.80(4H,m,4CH); 3.50–3.40(1H,m,CH); 3.40–3.30(1H,d,CH); 2.82(6H,s, 2CH$_3$); 2.60–2.50(1H,d,CH); 2.40–2.20(1H, m, CH); 2.10–1.90(2H,m,2CH); 1.80–1.70(2H,m,2CH); 1.50–1.40 (1H,d,CH); 1.40–1.20(1H,m,CH); 1.10(3H,s,CH$_3$); 0.80 (3H,s,CH$_3$).

Elemental Analysis=meets standards for C$_{15}$H$_{27}$NO$_5$S

Step (c)—Preparation of: (1R)-camphor-2-(1-methanesulfonyl)-spirochetal glycerol-10-sulfonyldimethylamine The product was synthesised according to the processes described in Example 1, step (c), with a yield of 90%.

TLC=hexane/AcOEt 7:3, Rf=0.25

$[\alpha]_D$=+13.50 (1% CHCl$_3$)

$^1$H-NMR-300 Mhz (CDCl$_3$); δ4.60–4.50(1H,m,CH); 4.35–4.20(2H,m,2CH); 4.10–4.00(1H,t,CH); 3.75–3.65(1H, t,CH); 3.25–3.15(1H,d,CH); 3.10(3H,s,CH$_3$); 2.85(6H,s, 2CH$_3$); 2.60–2.50(1H,d,CH); 2.35–2.20(1H,m, CH); 2.10–2.00(1H,m,CH); 1.90–1.70(3H,m,3CH); 1.50–1.40 (1H,d,CH); 1.40–1.20(1H,m,CH); 1.05(3H,s,CH$_3$); 0.90 (3H,s,CH$_3$)

Elemental Analysis=meets standards for C$_{16}$H$_{29}$NO$_7$S$_2$

Step (d)—Preparation of: (1R)-camphor-2-(1-trimethylammonium)-spirochetal glycerol-10-sulfonyldimethylamine methanesulfonate The product was synthesised according to the processes described in Example 1, step (d), with a yield of 98%.

TLC=CHCl$_3$/IsPrOH/MeOH/H$_2$O/CH$_3$COOH (4.2/0.7/ 2.8/1.05/1.05)

Rf=0.60

$[\alpha]_D$=−8.85° (1% MeOH)

$^1$H-NMR-300 Mhz (MeOD); δ4.65–4.55(1H,m,CH); 4.35–4.20(1H,t,CH); 3.85–3.75(1H,dd,CH); 3.75–3.65(1H, t,CH); 3.51–3.50(1H,d,CH); 3.40–3.2 (2H,m,2CH); 3.50 (9H,s,3CH$_3$); 2.70(3H,s,CH$_3$); 2.40–2.20(1H,m,CH); 2.15–2.05(1H,m,CH); 1.90–1.75(2H,m,2CH); 1.60–1.50 (1H,d,CH); 1.40–1.30(1H,m,CH); 1.05(3H,s,CH$_3$); 0.90 (3H,s,CH$_3$)

Fab-Ms=375

Elemental Analysis=meets standards for C$_{19}$H$_{38}$NO$_7$S$_2$

Step (e)—Preparation of: (R)-3-trimethylammonium-1,2-dihydroxy-propane methanesulfonate and Recovery of (1R)-camphor-10-sulfonyldimethylamine The product was synthesised according to the processes described in Example 1, step (e).

Stages (f)–(h)

The products were synthesised according to the processes described in Example 1, stages (f)–(h).

What is claimed is:

1. Process for the preparation of R-(−)-carnitine comprising the following steps:

(a) converting (−)camphorsulfonic acid chloride to (1R)-camphor-10-sulfonamide

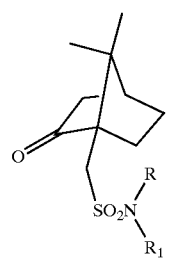

in which:

R and R₁, which may be the same or different, are hydrogen or C₁–C₄ alkyl benzyl but cannot be both hydrogen; or R and R₁, together with the nitrogen atom to which they are bonded, form a heterocyclic group with 4–6 carbon atoms;

by reacting

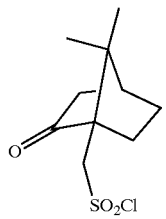

with an amine of the formula HNRR₁, in which R and R₁ are as indicated above, at a chloride:amine molar ratio from 1:1.1 to 1:1.5, at 0° C.–30° C. for 2–4 hours;

(b) condensing the sulfonamide prepared in step (a) with glycerol at a molar ratio from 2:1 to 5:1, in an acid medium, and obtaining (1R)-camphor-2-spirochetal glycerol-10-sulfonamide

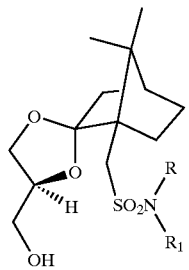

(c) reacting the sulfonamide of step (b) with methanesulfonyl chloride in a basic medium, at a molar ratio 1:1, at 0° C.–20° C., and obtaining (1R)-camphor-2-(1-methanesulfonyl)-spirochetal glycerol-10-sulfonamide

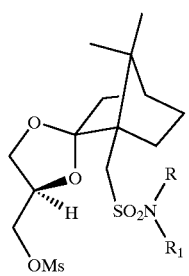

(d) substituting a trimethylammonium group for the mesyloxy group in step (c) by reacting the sulfonamide of step (c) with trimethylamine in an alcohol medium, at a sulfonamide:trimethylamine molar ratio from 1:20 to 1:1.5 at 25° C.–100° C., and obtaining (1R)-camphor-2-(1-trimethylammonium)-spirochetal glycerol-10-sulfonamide methanesulfonate

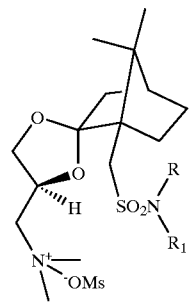

(e) hydrolyzing the methanesulfonate of step (d) in an acid medium, subsequently adding an organic solvent, and obtaining an aqueous phase containing (R)-3-trimethylammonium-1,2-dihydroxy-propane methanesulfonate

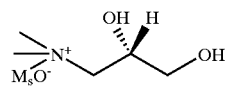

and an organic phase containing sulfonamide

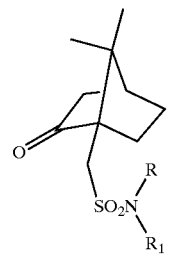

which is recycled to step (b);

(f) brominating the methanesulfonate of step (e) with hydrobromic acid in acetic acid, at a methanesulfonate:HBr molar ratio from 1:6 to 1:1, for 15–24 hours at room temperature, subsequently adding an C₁ alkanol and refluxing the resulting mixture for 4–8 hours and then drying the mixture, and obtaining (R)-3-trimethylammonium-1-bromo-2-hydroxy-propane bromide

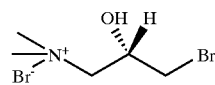

(g) converting the propane bromide of step (f) to (R)-carnitine nitrile bromide

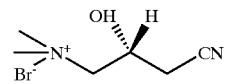

by reacting an aqueous solution of the propane bromide with an equimolar amount of an alkaline cyanide for 5–24 hours at 25° C.–80° C. and then concentrating to dryness;

(h) converting the nitrile bromide of step (g) to R-(−)-carnitine inner salt by
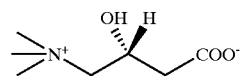
reacting the nitrile bromide with a concentrated acid at 60° C.–100° C. for 2–6 hours, then
(i) diluting the reaction mixture with water and eluting an aqueous solution thus obtained first on a basic ion-exchange resin.
* * * * *